(12) United States Patent
Mazur

(10) Patent No.: US 11,506,193 B2
(45) Date of Patent: *Nov. 22, 2022

(54) AEROSOL-GENERATING DEVICE

(71) Applicant: Altria Client Services LLC, Richmond, VA (US)

(72) Inventor: Ben Mazur, Bristol (GB)

(73) Assignee: Altria Client Services LLC, Richmond, VA (US)

( * ) Notice: Subject to any disclaimer, the term of this patent is extended or adjusted under 35 U.S.C. 154(b) by 186 days.

This patent is subject to a terminal disclaimer.

(21) Appl. No.: 16/993,486

(22) Filed: Aug. 14, 2020

(65) Prior Publication Data

US 2020/0370547 A1    Nov. 26, 2020

Related U.S. Application Data

(63) Continuation of application No. 16/241,043, filed on Jan. 7, 2019, now Pat. No. 10,746,167, which is a
(Continued)

(30) Foreign Application Priority Data

Aug. 16, 2016  (EP) .................................... 16184283

(51) Int. Cl.
*A24F 47/00* (2020.01)
*F04B 43/02* (2006.01)
(Continued)

(52) U.S. Cl.
CPC ............ *F04B 43/026* (2013.01); *A24F 40/48* (2020.01); *A24F 40/485* (2020.01);
(Continued)

(58) Field of Classification Search
CPC ....... A24F 40/48; A61M 15/06; F04B 43/026; F04B 43/046
See application file for complete search history.

(56) References Cited

U.S. PATENT DOCUMENTS

2002/0114716 A1  8/2002  Takagi et al.
2004/0000843 A1  1/2004  East
(Continued)

FOREIGN PATENT DOCUMENTS

EA    009532 B1   2/2008
EP   2222959 B1   1/2012
(Continued)

OTHER PUBLICATIONS

Extended European Search Report dated Nov. 18, 2021 for corresponding European Application No. 21192328.9.
(Continued)

*Primary Examiner* — Eric Yaary
(74) *Attorney, Agent, or Firm* — Harness, Dickey & Pierce, P.L.C.

(57) ABSTRACT

An aerosol-generating device includes a pump. The pump includes a first pump chamber and a second pump chamber on opposing sides of a separation element. Each of the first pump chamber and the second pump chamber have an inlet valve and an outlet valve configured to establish a pumping direction. The pump also includes a first actuator and a second actuator. The first actuator is associated with the first pump chamber and the second actuator is associated with the second pump chamber. The first actuator and the second actuator are each configured to change a chamber volume of the respective pump chamber. The pump further includes a common inlet, and a common outlet. The common inlet and common outlet are in fluid communication with the first pump chamber and the second pump chamber and are configured to establish a flow direction. The pumping direction is aligned with the flow direction.

20 Claims, 2 Drawing Sheets

Related U.S. Application Data continuation of application No. 15/675,164, filed on Aug. 11, 2017, now Pat. No. 10,174,749, which is a continuation of application No. PCT/EP2017/068691, filed on Jul. 24, 2017.

(51) Int. Cl.

| | | |
|---|---|---|
| *A61M 15/00* | (2006.01) | |
| *A61M 15/06* | (2006.01) | |
| *A24F 40/48* | (2020.01) | |
| *A24F 40/485* | (2020.01) | |
| *F04B 43/04* | (2006.01) | |
| *A61M 11/00* | (2006.01) | |
| *A61M 11/04* | (2006.01) | |
| *A24F 40/10* | (2020.01) | |

(52) U.S. Cl.
CPC ........ *A61M 15/0065* (2013.01); *A61M 15/06* (2013.01); *F04B 43/046* (2013.01); *A24F 40/10* (2020.01); *A61M 11/005* (2013.01); *A61M 11/042* (2014.02); *A61M 15/0085* (2013.01)

(56) References Cited

U.S. PATENT DOCUMENTS

| | | |
|---|---|---|
| 2009/0242060 A1 | 10/2009 | Chen et al. |
| 2011/0005606 A1 | 1/2011 | Bartels et al. |
| 2014/0060554 A1 | 3/2014 | Collett |
| 2015/0117842 A1 | 4/2015 | Brammer et al. |
| 2016/0213068 A1 | 7/2016 | Hon |
| 2016/0262443 A1 | 9/2016 | Piccirilli |
| 2016/0262457 A1 | 9/2016 | Borkovec |

FOREIGN PATENT DOCUMENTS

| | | |
|---|---|---|
| JP | 2013-514836 A | 5/2013 |
| JP | 2015-532828 A | 11/2015 |
| RU | 2097996 C1 | 12/1997 |
| RU | 2569796 C2 | 11/2015 |
| WO | WO-2007-111049 A1 | 10/2007 |

OTHER PUBLICATIONS

Japanese Office Action dated Oct. 4, 2021 for corresponding Japanese Application No. 2019-508944, and English-language translation thereof.
Russian Notice of Allowance dated May 20, 2021 for corresponding Russian Application No. 2019107172, and English-language translation thereof.
European Search Report for European Application No. EP16184283 dated Feb. 7, 2017.
International Preliminary Report On Patentability for Application No. PCT/EP2017/068691 dated Jul. 25, 2018.
Written Opinion for International Application No. PCT/EP2017/068691 dated Oct. 26, 2017.
International Search Report for corresponding International Application No. PCT/EP2017/068691 dated Oct. 30, 2017.
Notice of Allowance dated May 9, 2022 issued in corresponding Japanese Patent Application No. 2019-508944.
Russian Office Action and Search Report dated Jul. 5, 2022 for corresponding Russian Application No. 2021121382, and English-language translation thereof.

AEROSOL-GENERATING DEVICE

CROSS-REFERENCE TO RELATED APPLICATIONS

This application is a continuation of U.S. application Ser. No. 16/241,043, filed on Jan. 7, 2019, which is a continuation of U.S. application Ser. No. 15/675,164, filed on Aug. 11, 2017, which is a continuation of, and claims priority to, international application no. PCT/EP2017/068691, filed on Jul. 24, 2017, and further claims priority under 35 U.S.C. § 119 to European Patent Application No. 16184283.6, filed Aug. 16, 2016, the entire contents of each of which are incorporated herein by reference.

BACKGROUND

Field

At least one example embodiment relates to an aerosol-generating device, such as an aerosol-generating device including a micropump.

Description of Related Art

In aerosol-generating devices a liquid may be vaporized and/or atomized in an atomizer. The atomizer may include a heating element arranged next to an opening of a reservoir containing the liquid. The liquid may be transported to the atomizer by capillary action of a capillary material.

SUMMARY

At least one example embodiment relates to an aerosol-generating device.

In at least one example embodiment, an aerosol-generating device comprises a reservoir configured to hold an aerosol-forming substrate, an atomizer configured to atomize the aerosol-forming substrate, and a micropump between the reservoir and the atomizer. The micropump is in fluid connection with the reservoir and the atomizer. The micropump is configured to supply the aerosol-forming substrate from the reservoir to the atomizer. The micropump includes two pump chambers, each of the two pump chambers having a chamber volume, and each of the two pump chambers including, at least one inlet valve, and at least one outlet valve. The at least one inlet valve and the at least one outlet valve are configured to establish a pumping direction. The micropump also includes two actuators, a common inlet, and a common outlet. Each of the two actuators is assigned to a respective one of the two pump chambers. Each of the two actuators is configured to change the chamber volume of the respective one of the two pump chambers. The two pump chambers are arranged in parallel and in fluid connection with the common inlet and the common outlet. The two actuators are configured to operate in parallel such that a volume change in each of the two pump chambers occurs simultaneously for both pump chambers.

In at least one example embodiment, the two pump chambers are in direct fluid connection with the common inlet and the common outlet.

In at least one example embodiment, each of the two pump chambers is arranged opposite to a respective one of the two actuators.

In at least one example embodiment, the two pump chambers and the two actuators are configured such that a same volume change in each of the two pump chambers occurs upon operation of the two actuators.

In at least one example embodiment, the chamber volume of each of the two pump chambers is identical.

In at least one example embodiment, a flow rate through the micropump ranges from about 1 µL/s to about 7 µL/s.

In at least one example embodiment, each of the two actuators is a piezo membrane actuator.

In at least one example embodiment, the micropump comprises two inlet valves and two outlet valves per pump chamber.

In at least one example embodiment, the micropump is generally symmetric about a plane arranged parallel to and between the two pump chambers.

In at least one example embodiment, an inlet connection of the common inlet and an outlet connection of the common outlet are at a same side of the micropump.

In at least one example embodiment, the aerosol-generating device further comprises a flow sensor connected to a control circuit, the control circuit configured to control a fluid flow in the micropump.

In at least one example embodiment, the atomizer comprises at least one of an acoustic atomization element, an ultrasonic vibrator, or a vaporizer. In at least one example embodiment, the vaporizer includes a heater.

In at least one example embodiment, the aerosol-forming substrate includes at least one of a nicotine containing aerosol-forming substrate or a tobacco flavour containing aerosol-forming substrate.

In at least one example embodiment, the aerosol-forming substrate is a viscous liquid having a viscosity ranging from about 1 mPas and 200 mPas. In at least one example embodiment, the viscous liquid has a viscosity ranging from about 1 mPas to about 150 mPas.

BRIEF DESCRIPTION OF THE DRAWINGS

Example embodiments will now be described, by way of example only, with reference to the accompanying drawings.

DETAILED DESCRIPTION

Figure 1:
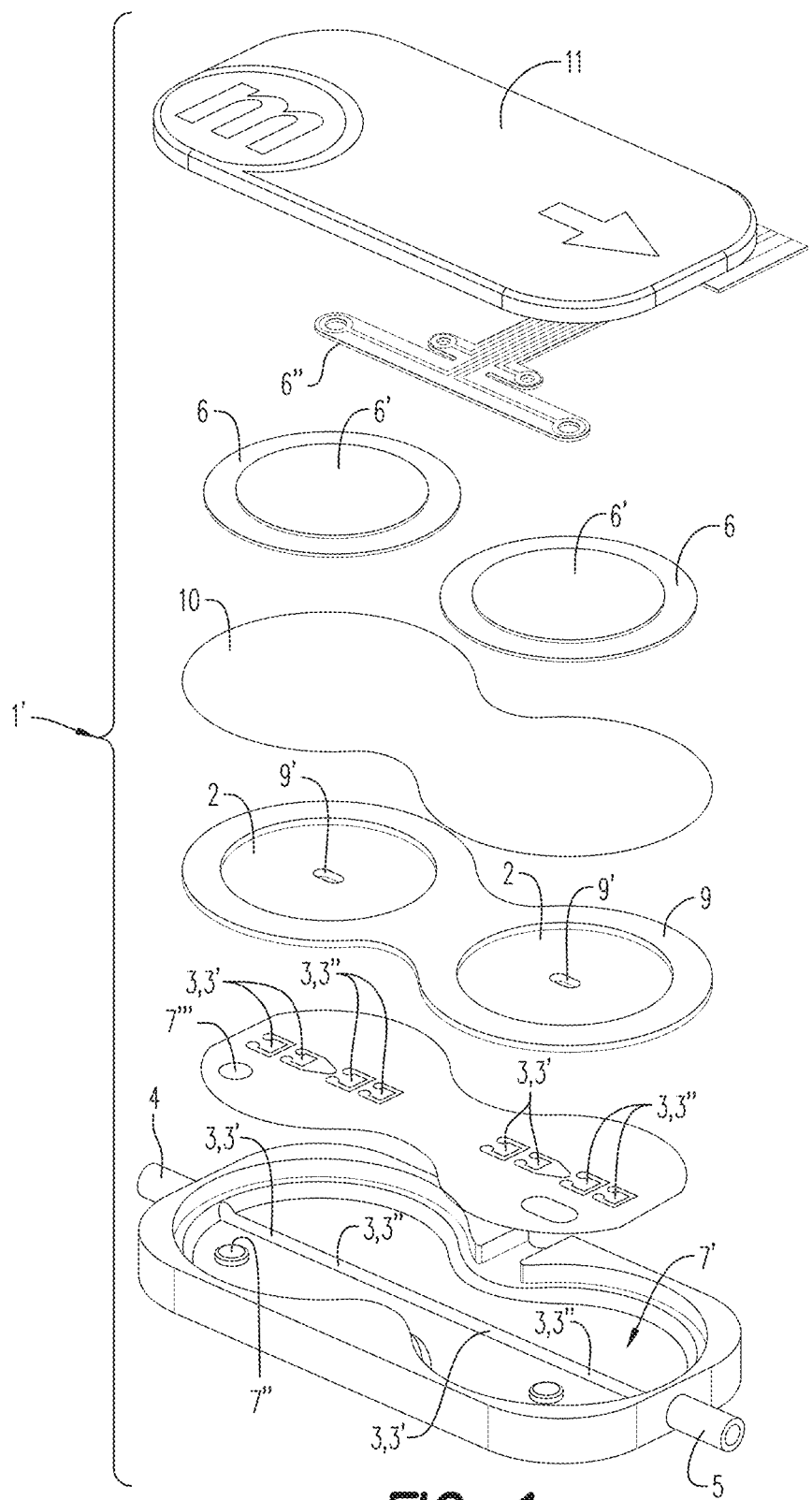
FIG. 1 is an exploded view of a micropump having two serially arranged actuators showing exemplary parts of the micropump according to at least one example embodiment.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

At least one example embodiment relates to an aerosol-generating device. The device comprises a reservoir configured to hold an aerosol-forming substrate and an atomizer configured to atomize the aerosol-forming substrate. The device further comprises a micropump between the reservoir and the atomizer and in fluid connection with the reservoir and the atomizer. The micropump is configured to supply the aerosol-forming substrate from the reservoir to the atomizer. The micropump comprises two pump chambers having two separate chamber volumes and two actuators. Each actuator is assigned to one of the two pump chambers for changing a respective chamber volume. Each pump chamber is provided with at least one inlet valve and at least one outlet valve, which are configured to establish a pumping direction. The micropump further comprises a common inlet and a common outlet. The two pump chambers are arranged in parallel and are in fluid connection with the common inlet and the common outlet. The actuators are configured to operate in parallel such that a volume change in each of the two pump chambers occurs substantially simultaneously for both pump chambers. In at least one example embodiment, control electronics present in the aerosol-generating device may control the micropump and/or the actuators of the micropump respectively.

By operating the actuators substantially simultaneously, and having substantially same volume changes by an actuator stroke of each of the actuators, a pumping pressure may basically be doubled compared to having only one pumping chamber. A pumping pressure may also be substantially doubled compared to, for example, two pumps connected in series. Such single or serial micropumps are available from Bartels Mikrotechnik GmbH, with the Bartels mp5 micropump having one actuator and the Bartels mp6 micropump having two actuators in two serially arranged pump chambers.

Arranging two pump chambers in parallel also allows for a substantially high performance of the micropump and high flow rates of viscous fluids. Since increased and/or maximum flow rates typically decrease with higher viscosity fluids, two pump chambers at higher pumping pressure allow for well-defined high flow rates also for viscous or high viscous fluids.

A parallel arrangement of two pump chambers also facilitates a compact and small design of the micropump and of the aerosol-generating device the micropump is used in. This is in particular suitable for hand-held devices, where space is limited and the device should be miniaturized. Such hand-held devices may, for example, be inhalators for medical purposes or vaping or smoking devices. Such hand-held devices may, for example, be vaping devices wherein an e-liquid is vaporized, and the e-liquid is viscous.

The actuators of the micropump may be driven by control electronics connected to the micropump. The control electronics may be combined with control electronics of the aerosol-generating device the control the aerosol-generating device.

The actuators may be piezo membrane actuators, mechanical actuators, thermal actuators, magnetic actuators, or other suitable actuators that result in a volume change of a pump chamber. In at least one example embodiment, disk- or plate-shaped actuators are used. In at least one example embodiment, two piezo membrane actuators are used in the micropump.

In piezo membrane actuators, the amplitude of the voltage applied to the actuator defines the strokes of the actuator and therefore the displacement of the pumped medium per pump cycle. With rising amplitude of a controller voltage, the flow rate rises substantially linearly to a desired and/or maximum flow rate.

The flow rate also increases linearly in a defined frequency range. The frequency determines the number of pump strokes per unit of time. After reaching a desired and/or a maximum flow rate at the resonance frequency, the flow rate decreases again with higher frequencies above the resonant point.

The combination of signal, amplitude and frequency defines the performance of the micropump. Operation parameters may be chosen based on the fluid to be transported by the micropump.

Each pump chamber of the micropump comprises at least one inlet valve and at least one outlet valve. In at least one example embodiment, each pump chamber comprises two inlet valves and two outlet valves. Two valves per pump chamber may provide a high reliability of operation of the micropump.

In operation, a fluid, such as the aerosol-generating substrate, flows along a fluid path from the common inlet towards the common outlet, and through each of the two pump chambers via their respective inlet valves and outlet valves. That is, the fluid path can be defined as a route or a trajectory the fluid follows as it is being transported in the micropump. In at least one example embodiment, the valves are arranged and designed in such a manner that direction changes of a fluid stream along the fluid path being invoked by the valves are reduced and/or minimized. Thus, energy for the transport of the fluid is reduced and/or minimized and additionally, the settling of gas bubbles is reduced. Moreover, a smoother fluid path may reduce turbulence and lessen the amount of fluid impingement upon the walls of the micropump, thereby helping to reduce the amount of mechanical vibration and noise. In at least one example embodiment, changes of angles in the fluid path are not abrupt. In at least one example embodiment, the fluid path comprises no angles of 90 degree or smaller. In at least one example embodiment, the design of the pump chambers and their respective valves ensures that the fluid flows through the valves at an obtuse angle. In at least one example embodiment, the direction of flow of fluid from the common inlet to the common outlet, along the fluid path, does not change by 90 degrees or more. In at least one example embodiment, holes in device elements of the micropump connecting different fluid planes comprise diameters equal to or larger than a length of the holes.

In at least one example embodiment, the two pump chambers are in direct fluid connection with the common inlet and with the common outlet. Thus, each pump chamber is directly connected to the common inlet and the common outlet without intermediate fluid channels. In at least one example embodiment, the fluid connections of the pump chambers and common inlet or common outlet are separated solely by the at least one inlet valve or the at least one outlet valve, respectively, of the pump chambers.

In the device the two pump chambers as well as the two actuators may be arranged substantially opposite each other. In at least one example embodiment, the two actuators and the two pump chambers are arranged exactly opposite each other. Such an arrangement facilitates the manufacture of the micropump and allows for the manufacture of a very compact micropump.

The two pump chambers and the two actuators may be configured such that a same volume change in each of the two pump chambers occurs upon operation of the two actuators.

The chamber volumes of the two pump chambers do not have to have a same size and may be different. However, in at least one example embodiment, the chamber volumes of the two pump chambers are identical.

In at least one example embodiment, the components which are required for the production of one pump chamber of the micropump, particularly the valve(s) and the actuator are designed to be substantially interchangeable with, or identical to the components for the second pump chamber of the same micropump. That is, all actuators, valves and optionally other components that are present in one pump chamber are designed identical to those of the other pump chamber. By this, the risk of confusion during assembly is reduced and the production cost may be reduced and/or minimized.

In at least one example embodiment, the micropump comprises a symmetric set-up in view of a plane arranged parallel to and between the two pump chambers.

A symmetric and in particular an identical set-up of the two pump chambers allow for a simplified control and operation of the micropump.

This symmetric set-up may include the common inlet and common outlet. Thus an inlet connection of the common inlet may be arranged at one side of the micropump and an outlet connection of the common outlet may be arranged at an opposite side of the micropump. However, an inlet connection of the common inlet and an outlet connection of the common outlet may also be arranged at a same side of the micropump. This allows the manufacture of an even more compact micropump.

In at least one example embodiment, all components which are in contact with the fluid consist of a same material. In at least one example embodiment, the pump chambers, valves, and common inlet and outlet are manufactured from a same material. Such a material may be adapted to the physical and chemical characteristics of a fluid to be pumped. In at least one example embodiment, all components which are in contact with the fluid may consist of polyphenylene sulphone (PPSU). This material is useful for the joining and fabrication techniques that may be used to install the micropump in the device. Other suitable materials may be used, for example polypropylene (PP) or polyimide (PI). In at least one example embodiment, the parts that are in contact with the fluid may be coated, for example, by biocompatible or other particularly inert materials, in order to adapt the device to specific requirements. Also other materials such as silicon, metals, and/or glasses may be used, wherein it should be ensured in the case of materials having only a low stretchability that the actuators can still lead to a change of the chamber volume.

All components of the micropump that must be joined to each other can for example be joined by suitable adhesives or by laser welding. The latter technique is suitable in particular for the joining of plastics and offers, short production times, and the possibility of producing a shermetically tight connection without adhesives that comes close to the strength of the source material.

In at least one example embodiment, the micropump comprises the following elements, which sequence basically corresponds to an assembly sequence. The micropump comprises two base elements each comprising a recess and half of an inlet and half of an outlet, two actuators with electrodes and electric terminals, each of the actuators arranged in one of the recesses, two protection layers arranged over each of the actuators, the protection layers each forming one side of a pump chamber, valve foils which are insertable into the recesses and which carry the movable parts of the inlet and outlet valves of the pump chambers, and two intermediate layers which are also insertable into the recesses and which have openings which form the immobile parts of the inlet and outlet valves. The intermediate layers form together with the respective protection layers and recess side walls the pump chambers.

Actuator and protection foil as well as valve foil and intermediate foil may be kept in place by seals, for example by weld seals or an adhesive seal.

Upon positioning of a flow separation element at a position in between the inlet and outlet and in between the two base elements, the two base elements may be put together and assembled. In at least one example embodiment, the two base elements are provided with a fluid-tight sealing formed by laser welding, and the recesses of the two base elements are closed in such a manner that the components in the interior of the base elements are protected from environmental influences. Upon assembly, each of the two halves of the inlet and outlet are also combined and form the common inlet and the common outlet, and the corresponding inlet connection and the outlet connection, which allow the micropump to connect to a reservoir and to the atomizer or to corresponding tubings connected to the reservoir and to the atomizer, respectively.

The aerosol-generating device may further comprise a flow sensor configured to control a fluid flow in the common outlet of the micropump. The flow sensor is connected to the control electronics which are configured to control the fluid flow by, for example, keeping the fluid flow constant, and/or by changing the micropump parameters if required. The device may thus comprise a controlled loop system.

The atomizer of the device may be designed to atomize and/or vaporize the aerosol-forming substrate by any suitable means, mechanisms, and/or methods. In at least one example embodiment, the atomizer may vaporize the aerosol-forming substrate by heat, and/or may atomize or nebulize the aerosol-forming substrate by ultrasound or other vibration means. The atomizer may comprise any one or a combination of an acoustic atomization element, an ultrasonic vibrator, a vaporizer such as a heater or any other atomizer.

The device may comprise any fluid to be atomized. The aerosol-forming substrate may be gas or liquid or a combination thereof. In at least one example embodiment, the aerosol-forming substrate is a liquid. However, the aerosol-forming substrate may originally also be a solid, which is liquefied, for example by heating, such that the liquid may be transported by the micropump to the atomizer.

The aerosol-forming substrate may, for example, comprise medicine, flavour or stimulating substances.

Liquid aerosol-forming substrate may comprise at least one aerosol former and a liquid additive.

The aerosol-former may, for example, be propylene glycol or glycerol.

The liquid aerosol-forming substrate may comprise water.

In at least one example embodiment, the aerosol-forming substrate is an e-liquid to be used in vaping systems.

In at least one example embodiment, the liquid additive may be any one or a combination of a liquid flavour or liquid stimulating substance. Liquid flavour may, for example, comprise tobacco flavour, tobacco extract, fruit flavour or coffee flavour. The liquid additive may, for example, be a sweet liquid such as for example vanilla, caramel and cocoa, a herbal liquid, a spicy liquid, or a stimulating liquid containing, for example, caffeine, taurine, nicotine or other stimulating agents known for use in the food industry.

The device comprises one or a combination of nicotine containing aerosol-forming substrate and tobacco flavour containing aerosol-forming substrate.

In at least one example embodiment, the device comprises a viscous liquid aerosol-forming substrate having a viscosity ranging from about 1 mPas to about 200 mPas, about 1 mPas to about 150 mPas, or about 80 mPas to about 130 mPas.

In at least one example embodiment, the aerosol-generating device is an electronic smoking device as used in electronic smoking systems or an electronic vaping device. The smoking device and/or the vaping device may be a hand-held device. The device may be a smoking system wherein tobacco is heated rather than combusted.

In at least one example embodiment, a chamber volume of the micropump ranges from about 1 ml to about 2 ml, a flow rate of the micropump ranges from about 1 µL/s to about 7 µL/s, a pumping pressure of the micropump ranges from about 500 mBar to about 700 mBar, and a size of the micropump (without connectors) is about 14×14×6.5 mm$^3$.

In at least one example embodiment, the micropump has a frequency ranging from about 0 Hz to about 300 Hz, and a peak-to-peak voltage of up to about 320 Vpp. The micropump may have a sinusoidal, rectangular, or intermediately shaped actuator voltage curve. In at least one example embodiment, lifting and lowering phases of the actuator are not identical. In at least one example embodiment, an actuator voltage curve is adapted in order to improve and/or optimize the micropump in view of noise and bubble generation at a given flow rate and viscosity of a fluid.

FIG. 1 is an exploded view of a micropump having two serially arranged actuators showing exemplary parts of the micropump according to at least one example embodiment.

FIG. 1 is an exploded view of a Bartels mp6 micropump as described in US patent application US 2011/0005606, the entire content of which is incorporated herein by reference thereto. The micropump 1' includes a layered assembly, which comprises two serially arranged pump chambers 2. In FIG. 1, the assembly 1' includes the following components: a base element 7, a valve foil 8, an intermediate layer 9, a protection layer 10, two actuators 6 and a lid element 11.

The base element 7 is made of a plastic. The base element 7 comprises a recess 7' into which all subsequent components are inserted. The base element 7 also includes inlet 4 and exit 5 which are provided for the delivery of the fluid, and which, as depicted here, are for example designed as a hose-like connector. Other connector types which are adapted to the respective application may be used. The base element 7 also comprises parts of the fluid channels for the valves 3, which are produced by injection moulding, and therefore, in the same process as the base element itself. The base element 7 includes projecting parts 7" having a same shape as mounting aids 7''', which are arranged in such a manner that they cooperate with the recesses of the mounting aid 7'''. The assembly of subsequent components such as the valve foil 8 can only occur in one certain way, so that an incorrect mounting is excluded to a large extent.

The valve foil 8 includes the movable parts of the valves 3. The valve foil 8 is inserted into the base element 7. In at least one example embodiment, the valve foil 8 comprises the movable parts of the inlet valves 3' of each pump chamber, as well as the movable parts of the respective outlet valves 3". Furthermore, the valve foil 8 also comprises the recesses of the mounting aid 7''' which aid in the insertion of the valve foil 8 into the base element 7.

The intermediate layer 9 is made of plastic, and is designed in such a manner that it can be inserted into the recess 7' of the base element 7. In the centre of each pump chamber 2, which is respectively formed by a recess in the intermediate layer, one respective opening 9' is located through which fluid can flow into the respective pump chamber and/or out of the same.

The protection layer 10 is applied onto the intermediate layer and thus fluidically borders the pump chamber. The protection layer should be firmly connected with the intermediate layer 9, so that fluid cannot exit or flow over a circumference thereof nor in the region between the pump chambers. In at least one example embodiment, penetration laser welding is used to connect the protection layer 10 and the intermediate layer 9. Alternative production techniques may include gluing, ultrasound welding, or mechanical clamping of the respective components.

Two actuators 6 are provided as disc shaped piezo-actuators in the example embodiment shown. Each of the actuators is geometrically adapted to the pump chamber 2 which is arranged below, and the actuators include electrodes 6' for establishing electrical connections. Connected to these is an electric terminal 6" which can be led out of the housing of the assembly 1', and which provides a sufficient number of individual wires for the connection of each actuator 6.

The lid element 11 serves as a seal of the housing of the apparatus. The lid element 11 covers at portion of the base element 7. In at least one example embodiment, the lid element 11 is also fabricated from plastic and is designed such that it can be connected with the base element 7 by penetration laser welding.

Figure 2:
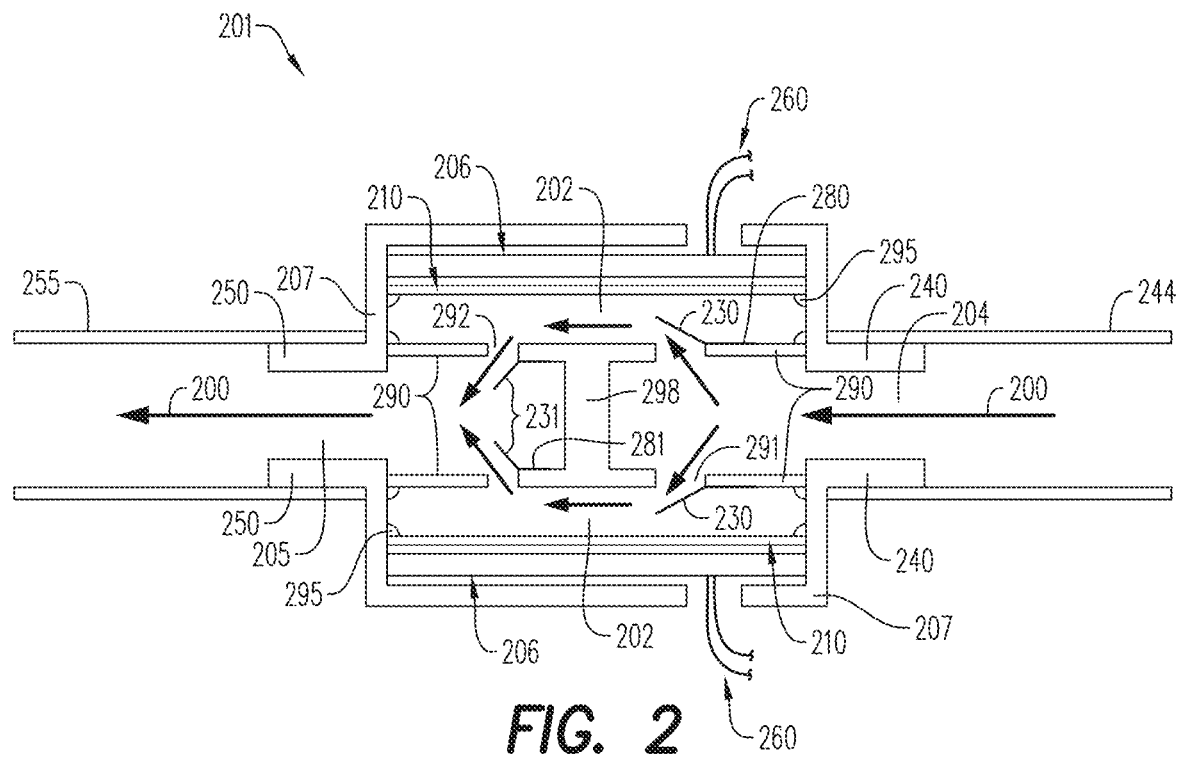
FIG. 2 is an illustration of a micropump with parallel actuators according to at least one example embodiment.

FIG. 2 is an illustration of a micropump with parallel actuators according to at least one example embodiment.

In at least one example embodiment, as shown in FIG. 2, a micropump 201 with two actuators 206 arranged in parallel. The micropump 201 is a layered assembly, wherein the basic elements of one pump chamber may be similar or the same as one individual pump chamber and actuator as described with respect to FIG. 1.

In FIG. 2, two base elements 207 each comprise a recess into which all components forming one pump chamber are inserted. The two base elements 207 each include an inlet housing portion 240 and an outlet housing portion 250. When the two base elements 207 are assembled, the inlet housing portions 240 form a common inlet 204, and the outlet housing portions 250 form a common outlet 205. The inlet 204 and the outlet 205 may be connected to tubings 244, 255, for example plastic hoses, for the delivery of fluid to the micropump and away from the micropump 201.

In at least one example embodiment, the two actuators 206 are disc shaped piezo-actuators. One actuator is inserted into a recess of a respective base element 207. The piezo-actuators may, for example, be a piezo ceramic mounted on a brass membrane, which piezo ceramic deforms the membrane when a voltage is applied to the piezo ceramic.

Each of the actuators 206 is sized and configured to mate fit within the geometry and size of the recess into which each actuator 206 is placed, and which basically defines the lateral extensions of the pump chambers 202, which are arranged below or above each actuator 206. The actuators 206 are connected to electrodes and comprise wiring 260 to form electrical contacts of the actuators. The wiring 260 leads out of the housing of the micropump 201.

The micropump also includes two protection layers 210, for example a Kapton tape, which are provided in the recess of each base element 207. Each protection layer 210 forms one side of a pump chamber 202. The protection layer 210 transmits movement of the piezo actuator into the pump chamber 202. The protection layer 210 is held in place by a seal 295, for example a weld seal, clamping, or an adhesive seal, also sealing the pump chamber 202.

An intermediate layer 290, which may be formed of plastic, is inserted into each of the respective recesses of the base elements 207. The intermediate layers 290 carry the valve foils and are held in place by another seal 295, such as for example a weld seal, also sealing the pump chamber 202. The space between intermediate layer 290 and protection layer 210 and the recess walls defines the size of the pump chamber 202.

Off center in the intermediate layer 290 in the direction of the inlet 204, an inlet opening 291 is located, through which fluid can flow from the common inlet 204 into the respective pump chamber 202. Off center in the intermediate layer 290 into the direction of the outlet 205 an outlet opening 292 is located, through which fluid can flow from the respective pump chamber 202 into the common outlet 205. In the center of the intermediate layer 290 a flow separation element 298 is arranged.

One flow separation element 298 is used for both pump chambers, and is arranged between the two pump chambers separating the common inlet 204 from the common outlet 205 in view of a flow direction. A flow of fluid 200 from the common inlet 204 towards the common outlet 205 defines a fluid path, shown as the arrows in FIG. 2. The fluid path is shown comprising no angles of 90 degree or smaller, i.e. the flow path comprises only obtuse angles, because the flow separation element 298 has a shape and structure to support a smooth fluid flow from the common inlet 204 through the inlet valves 230 and from the outlet valves 231 into the common outlet 205.

A first valve foil 280 comprises the movable parts of the inlet valve or valves 230 of each pump chamber 202. A second valve foil 281 comprises the movable parts of the respective outlet valves 231. The first valve foil 280 may be attached to the intermediate layer 290. The second valve foil 281 may be attached to the flow separation element 298.

By parallel and synchronous actuation of the piezo actuators 206, a deformation draws back the protective foils 210. Due to the generated pressure change upon a draw on the aerosol-generating device, the inlet valves 230 open, and the fluid flows from the common inlet 204 to pass into the respective pump chambers 202. An actuation of the piezo actuators into the opposite direction compress the pump chambers 202 due to the flexibility of the protective layers 210 and push the fluid from the pump chambers 202 through the pushed open outlet valves 231 out of the pump chambers 202 and into the common outlet 205. Due to the arrangement of the valves, inlet valves 230 are automatically closed when outlet valves 231 are opened and vice versa.

In at least one example embodiment, the pump chambers 202 have a same chamber volume and a same chamber geometry.

The micropump 1 of FIG. 1 is symmetric with respect to a virtual middle plane arranged between and parallel to the two actuators 6, and extending through the common inlet and common outlet. Such a construction allows the manufacture of the micropump with few parts only, by two identical individual micropump halves comprising one base element and pump chamber.

Figure 3:
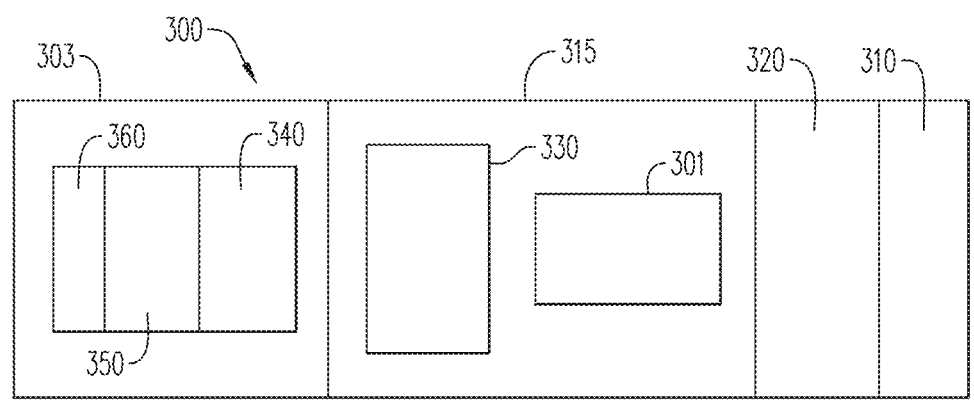
FIG. 3 is a schematic view of an aerosol-generating system including a micropump according to at least one example embodiment.

FIG. 3 is a schematic view of an aerosol-generating device including a micropump according to at least one example embodiment.

In at least one example embodiment, an aerosol-generating device 300 includes a cartridge 315 and a battery section 305. The cartridge 315 may include a mouthpiece 310, a reservoir 320 configured to contain the aerosol-forming substrate, the micropump 301, and an atomizer 330. The micropump 301 may be the micropump of FIG. 1 or FIG. 2. The battery section 305 includes a battery 340, control circuitry 350, and a sensor 360.

In at least one example embodiment, in use, a draw is taken on the mouthpiece 310. The sensor 360 senses the draw. The control circuitry 350 then activates the micropump 1 and/or the atomizer 330. The micropump is configured to supply the aerosol-forming substrate from the reservoir to the atomizer. The micropump includes two pump chambers, each of the two pump chambers having a chamber volume, and each of the two pump chambers including, at least one inlet valve, and at least one outlet valve. The at least one inlet valve and the at least one outlet valve are configured to establish a pumping direction. The micropump also includes two actuators, a common inlet, and a common outlet. Each of the two actuators is assigned to a respective one of the two pump chambers. Each of the two actuators is configured to change the chamber volume of the respective one of the two pump chambers. The two pump chambers are arranged in parallel and in fluid connection with the common inlet and the common outlet. The two actuators are configured to operate in parallel such that a volume change in each of the two pump chambers occurs simultaneously for both pump chambers.

The specific example embodiments described above illustrate but do not limit the invention. It is to be understood that other example embodiments may be made and the example embodiments described herein are not exhaustive.

I claim:

1. An aerosol-generating device comprising:

a pump including, a first pump chamber and a second pump chamber, each of the first pump chamber and the second pump chamber having an inlet valve and an outlet valve configured to establish a pumping direction, a common inlet, and a common outlet, the common inlet and the common outlet being in fluid communication with the first pump chamber and the second pump chamber and being configured to establish a flow direction, the pumping direction aligned with the flow direction.

2. The device of claim 1, further comprising:

a first actuator and a second actuator, the first actuator being associated with the first pump chamber and the second actuator being associated with the second pump chamber.

3. The device according to claim 2, wherein the first pump chamber and the second pump chamber are each arranged opposite to a respective one of the first actuator and the second actuator.

4. The device according to claim 2, wherein the first actuator is configured to operate in parallel with the second actuator.

5. The device according to claim 2, wherein the first pump chamber, the second pump chamber, the first actuator and the second actuator are configured such that generally a same volume change in each of the first pump chamber and the second pump chamber occurs upon operation of each of the first actuator and the second actuator.

6. The device according to claim 2, wherein the first actuator and the second actuator are piezo membrane actuators.

7. The device according to claim 1, wherein chamber volumes of the first pump chamber and the second pump chamber are generally identical.

8. The device according to claim 1, wherein a flow rate through the pump ranges from about 1 μL/s to about 7 μL/s.

9. The device according to claim 1, wherein the first pump chamber and the second pump chamber each includes two inlet valves and two outlet valves.

10. The device according to claim 1, wherein the pump is generally symmetric about a plane arranged parallel to and between the first pump chamber and the second pump chamber.

11. The device according to claim 1, wherein the first pump chamber and the second pump chamber are arranged in parallel.

12. The device according to claim 1, wherein an inlet connection of the common inlet and an outlet connection of the common outlet are at a same side of the pump.

13. The device according to claim 1, further comprising:

a flow sensor; and a control circuit configured to control a fluid flow in the pump based on output from the flow sensor.

14. The device according to claim 1, further comprising:

a reservoir configured to hold an aerosol-forming substrate; and an atomizer configured to vaporize, atomize, or both vaporize and atomize the aerosol-forming substrate, the pump disposed between the reservoir and the atomizer and in fluid communication with the reservoir and the atomizer.

15. The device according to claim 14, wherein the aerosol-forming substrate includes a nicotine containing aerosol-forming substrate, a tobacco flavour containing aerosol-forming substrate, or both a nicotine containing aerosol-forming substrate and a tobacco flavour containing aerosol-forming substrate.

16. The device according to claim 14, wherein the aerosol-forming substrate is a viscous liquid having a viscosity ranging from about 1 mPas and 200 mPas.

17. The device according to claim 16, wherein the viscous liquid has a viscosity ranging from about 1 mPas to about 150 mPas.

18. The device according to claim 14, wherein the atomizer includes an acoustic atomization element, an ultrasonic vibrator, a vaporizer, or any combination thereof.

19. The device according to claim 18, wherein the atomizer includes the vaporizer, and the vaporizer includes a heater.

20. The device according to claim 1, wherein an inlet connection of the common inlet and an outlet connection of the common outlet are at different sides of the pump.

* * * * *